United States Patent
Crook et al.

[11] Patent Number: 5,853,395
[45] Date of Patent: Dec. 29, 1998

[54] EXTRACORPOREAL PNEUMOPERITONEUM ENCLOSURE AND METHOD OF USE

[75] Inventors: Berwyn M. Crook, Yardley; Robert D. Rambo, Sellersville; Thomas E. Lyons, Quakertown, all of Pa.; Frederic C. Feiler, Jr., Raleigh, N.C.

[73] Assignees: Dexterity, Inc., Blue Bell; Medical Creative Technologies, Inc., Chalfont, both of Pa.

[21] Appl. No.: 801,752

[22] Filed: Feb. 18, 1997

[51] Int. Cl.⁶ .............................. A61M 5/32; A61F 5/44
[52] U.S. Cl. ............................................. 604/174; 604/338
[58] Field of Search ................................. 604/174, 180, 604/338, 337; 606/201, 213, 215, 192; 600/207; 128/897, 850

[56] References Cited

U.S. PATENT DOCUMENTS

| | | |
|---|---|---|
| 4,069,913 | 1/1978 | Harrigan . |
| 4,436,519 | 3/1984 | O'Neill .................................. 604/175 |
| 4,485,490 | 12/1984 | Akers et al. . |
| 4,964,174 | 10/1990 | Martin .................................. 2/161 R |
| 5,082,005 | 1/1992 | Kaldany . |
| 5,366,478 | 11/1994 | Brinkerhoff et al. . |
| 5,370,625 | 12/1994 | Shichman . |
| 5,402,536 | 4/1995 | Matthews . |
| 5,437,683 | 8/1995 | Neumann et al. . |
| 5,480,410 | 1/1996 | Cuschieri et al. . |
| 5,522,791 | 6/1996 | Leyva . |
| 5,636,645 | 6/1997 | Ou . |
| 5,640,977 | 6/1997 | Leahy et al. . |
| 5,653,705 | 8/1997 | de la Torre et al. . |
| 5,672,168 | 9/1997 | de la Torre et al. . |
| 5,720,759 | 2/1998 | Green et al. ............................. 606/167 |
| 5,741,298 | 4/1998 | MacLeod ................................. 606/213 |

FOREIGN PATENT DOCUMENTS

9522289   8/1995   WIPO .

*Primary Examiner*—Wynn Wood Coggins
*Assistant Examiner*—Michael J Hayes
*Attorney, Agent, or Firm*—Howson and Howson

[57] ABSTRACT

Surgical apparatus for providing extracorporeal pneumoperitoneum. One embodiment provides a fluid and gas impremeable fingerless glove with a quick connect and disconnect assembly around the cuff of the glove which seals around an abdominal incision to allow hand-assisted minimally invasive surgery under conditions of pneumoperitoneum. Another embodiment provides a dome-shaped enclosure with the quick connect and disconnect assembly which seals around an abdominal incision to maintain pneumoperitoneum during interruptions in a surgical procedure.

30 Claims, 7 Drawing Sheets

EXTRACORPOREAL PNEUMOPERITONEUM ENCLOSURE AND METHOD OF USE

FIELD OF THE INVENTION

The present invention relates generally to an apparatus and method suitable for maintaining extracorporeal pneumoperitoneum at an abdominal fenestration during surgery, and more particularly to a quick connect and disconnect enclosure and method for insertion of instruments or a surgeon's hand into the body cavity through the fenestration for access to organs and instruments within the cavity without loss of insufflation pressure.

BACKGROUND OF THE INVENTION

Laparoscopy and endoscopy have become a preferred surgical procedure because it is minimally invasive of the patient's body and, in many instances, can be performed in short-procedure facilities with minimal trauma and significantly reduced recuperation time. In some cases, a new procedure referred to as hand-assisted laparoscopy, or endoscopy, has been employed in which a small muscle splitting incision is made just large enough for admitting the surgeon's hand into the abdominal cavity to enable palpation of organs and manipulation of surgical instruments, and to provide bio-physical feedback. Visual feedback is usually provided as well through an endoscope and TV monitor.

Several medical devices have been developed which make it possible for hand-assisted laparoscopy to be carried out in the abdominal cavity while under conditions of pneumoperitoneum. One device, for instance, by Patrick F. Leahy et al. disclosed in U.S. patent application Ser. No. 08/300,346 filed Mar. 29, 1995 (International Application PCT/US95/04202 published Oct. 29, 1995) provides a gas-tight sleeve which communicates with the abdominal cavity through an incision allowing the surgeon's hand access through entry and exit openings at opposite ends of the sleeve. The exit opening is sealed around the incision by a flange adhesively attached to the external surface of the abdomen. After the hand is passed through the entry opening, the sleeve is sealed around the surgeon's forearm by an adjustable cuff. A duckbill valve disposed between the entry and exit openings forms with the exit opening a substantially gas-tight chamber which allows the surgeon to withdraw his hand from the insufflated cavity with only a slight drop in gas pressure which can be quickly restored.

Another device disclosed in U.S. Pat. No. 5,480,410 to Cuschieri et al. provides a gas-tight enclosure in which a resilient ring at an exit opening is squeezed by hand into an oblong shape for insertion through the abdominal incision, then allowed to expand to its original shape under the edge of the incision to seal the peritoneum and enclosure for sufflation. At least one entry opening is provided for passing an instrument or a surgeon's hand into the enclosure. The enclosure may also include a surgical glove integrally sealed to the entry opening in a glove-box manner for allowing the surgeon's hand sterile access through the exit opening to organs and instruments within the abdominal cavity.

None of these devices, however, satisfies the need for such a gas-tight enclosure which can be quickly disconnected and reconnected as often as necessary during hand-assisted laparoscopic or endoscopic surgery while the enclosure remains sealed in place around the surgeon's hand, and which can maintain abdominal pneumoperitoneum during extended interruptions in an operation for other medical procedures.

SUMMARY OF THE INVENTION

Accordingly, it is an object of the present invention to provide a gas-tight extracorporeal pneumoperitoneum enclosure which is worn by the surgeon during hand-assisted laparoscopic or endoscopic surgery, which can be quickly disconnected from a patient as often as necessary in the course of an operation and reconnected while still sealed around the surgeon's hand, which allows the surgeon to manipulate or palpate organs and instruments from within the abdominal cavity, and which provides bio-physical feedback from the surgeon's hand under conditions of pneumoperitoneum.

Another object of the invention is to provide a surgical apparatus which can be continuously sealed around the surgeon's hand and forearm and selectively connected around an open wound while maintaining pneumoperitoneum in the course of a hand-assisted laparoscopic or endoscopic operation, and which will maintain pneumoperitoneum within the body cavity during any interruptions for any other medical procedure in the course of an operation.

A still further object of the invention is to enable minimally invasive surgery with minimal risk of damage to the immune system, shorter healing time and less time needed for recuperation in a hospital.

A further object is to provide a disposable surgical device which is relatively simple in design and easy to use and maintains dexterity of the hand.

These and other objects and novel features of the invention are accomplished in one embodiment of the extracorporeal pneumoperitoneum enclosure by a fluid and gas impermeable elongate fingerless glove enclosure with holes arranged to seal gas-tightly around the base of the surgeon's thumb and each of the fingers. A quick connect and disconnect assembly around the cuff of the glove gas-tightly seals to the skin around a fenestration allowing the surgeon to interrupt and resume a hand-assisted laparoscopic surgical procedure under conditions of pneumoperitoneum as often as needed without removing the sleeve from his/her hand. Integral with the quick connect and disconnect assembly is a pressure relief valve for preventing over-sufflation. At least one instrument port is provided in the cuff for admitting, without loss of gas pressure, surgical instruments.

In another embodiment of the extracorporeal pneumoperitoneum enclosure, a fluid and gas impermeable envelope is sealed gas-tightly around the incision. A quick connect and disconnect assembly with integral pressure relief valve is secured around an open base for maintaining the abdominal cavity sufflated during interruptions in an operation.

Upper and lower seal rings in both embodiments of the quick connect and disconnect assembly have respectively matching interfaces enabling the glove and envelope to be interchangeable without removing the lower seal ring previously attached to a patient. At least one instrument port may be provided in the envelope for accessing the body cavity through a fenestration.

The method for using the apparatus in a hand-assisted laparoscopic operation is as follows. A lower seal ring of the quick connect and disconnect assembly is adhesively sealed to the skin of the patient around the site where a small muscle-splitting incision is made through the abdomen wall and peritoneum. A wound liner and retractor may be inserted into the incision to protect the wound from contamination and to spread it apart for easier access. Wearing an inner surgical glove, the surgeon inserts his/her hand into the fingerless glove until the fingers extend completely through the holes and become tightly sealed around their bases. For extra precaution against leakage, an outer surgical glove is then placed over both the inner glove and the fingerless glove. An upper seal ring of the quick connect and disconnect assembly around the cuff of the glove is then sealingly interconnected with the lower seal ring and the abdomen and glove insufflated to the desired pressure either through a separate cannula or a port in the glove. The surgeon's hand may then be inserted into the abdominal cavity and removed as often as necessary during a laparoscopic procedure. A port in the cuff permits instruments to be inserted as often as needed. Any increase in sufflating gas pressure, caused by a sudden reduction in volume when inserting the hand, is prevented by the pressure relief valve in the quick connect and disconnect assembly.

Whenever the surgeon wishes to interrupt a surgical procedure while still maintaining pneumoperitoneum, the glove is disconnected from the lower seal ring, and in its place the dome-like envelope with upper seal ring are connected to the lower seal ring of the glove left on the abdomen and sufflation restored.

Other objects, advantages and novel features of the invention will become apparent from the following detailed description of the invention when considered in conjunction with the accompanying drawings.

DETAILED DESCRIPTION

Figure 1:
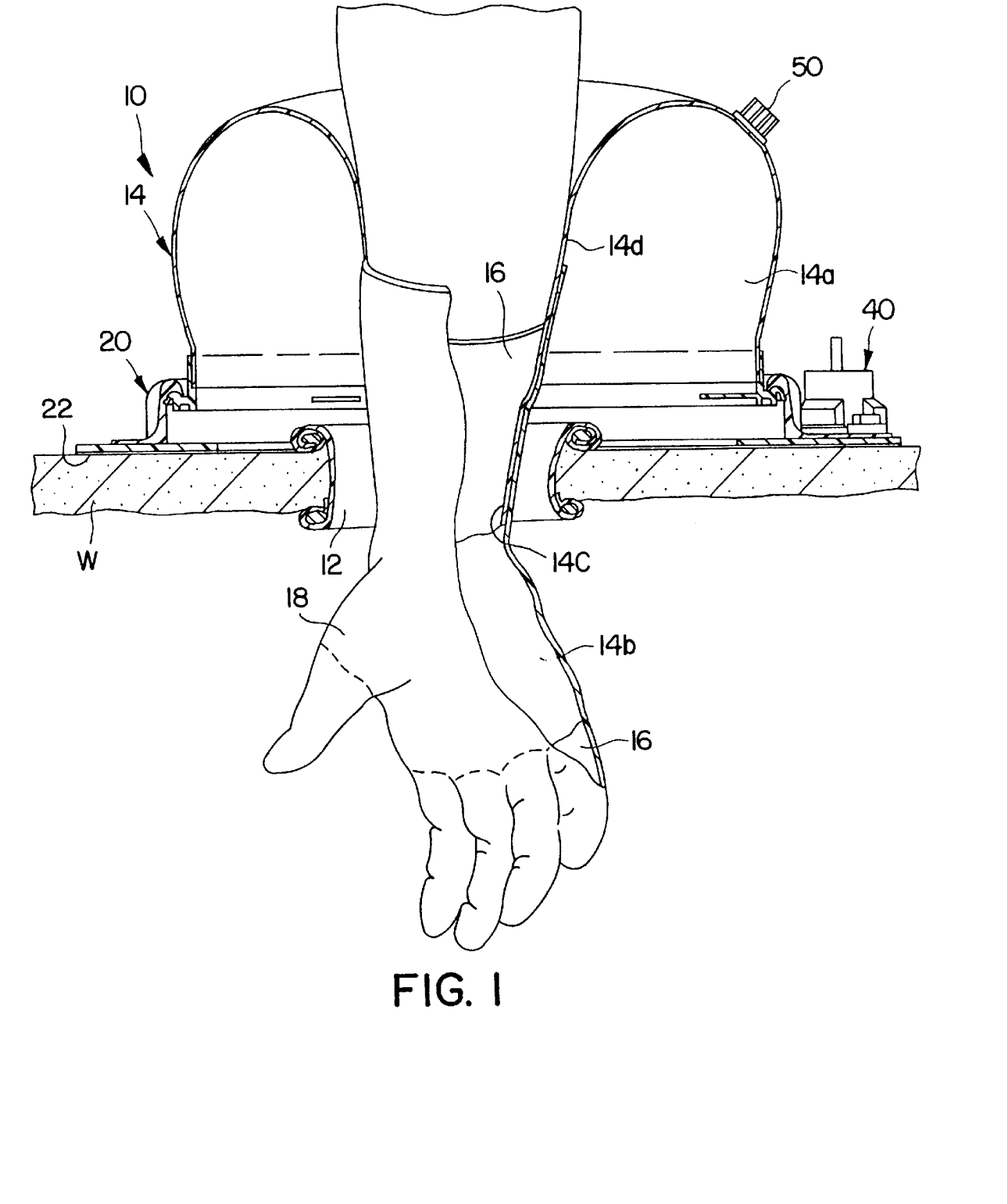
FIG. 1 is a view in elevation and partial cross section of an extracorporeal pneumoperitoneum enclosure according to one embodiment of the invention as applied in hand-assisted laparoscopic surgery in the abdomen.

Referring now to the drawings where like-referenced characters denote like or corresponding parts throughout the several views, FIG. 1 shows an extra-corporeal pneumoperitoneum glove enclosure 10 according to the invention applied to a patient's anterior abdominal wall W. A surgeon's hand extends into the abdominal cavity through a small muscle splitting incision which is protected from wound contamination by a wound protector/retractor 12 such as disclosed in U.S. Pat. No. 5,524,644 to Berwyn M. Crook.

Figure 2:
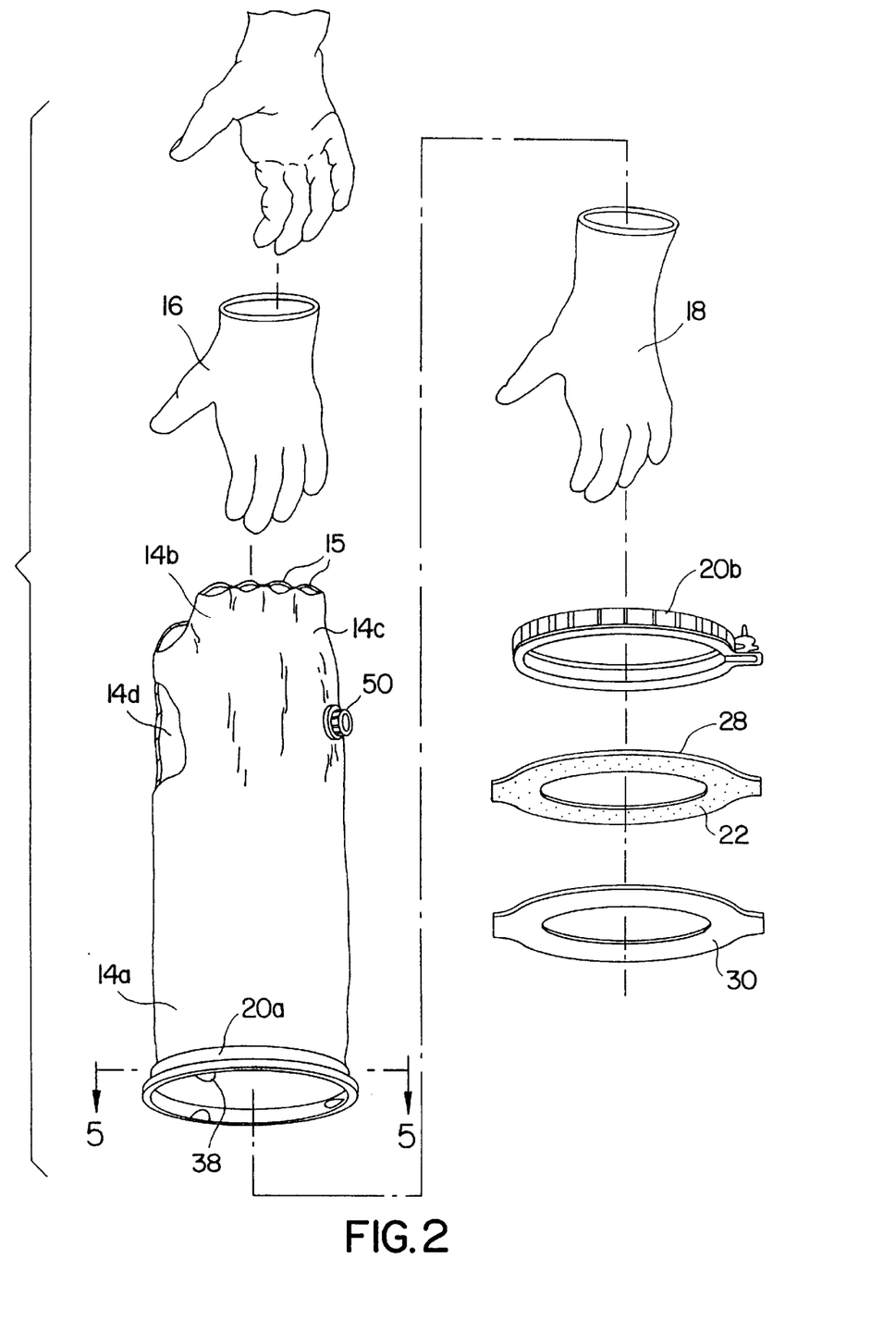
FIG. 2 is perspective view of various components of the enclosure of FIG. 1 spatially arranged in order of assembly.

In one preferred embodiment, enclosure 10 includes an elongate gas impermeable flexible glove 14 of sufficient length to receive the hand and forearm of the surgeon. Glove 14 extends from a proximal end cuff section 14a to a "fingerless," distal, hand section 14b and terminates with fingerholes 15 positioned to receive the full lengths of the surgeon's thumb and fingers and to seal the glove snugly around the root of each as shown in FIG. 2.

Glove 14 defines an inner side 14c which faces outward in FIG. 1 because cuff section 14a is inverted with the inside facing out. An inner surgical glove 16, worn in direct contact with the hand, is contiguous with inner side 14c, and an outer surgical glove 18, worn as extra precaution against leakage at fingerholes 15, covers an outer side 14d. Glove 14 is made of surgical grade supple transparent material in one size designed to seal around the fingers of a small hand but which will also stretch slightly under plastic deformation with residual elasticity to accommodate larger hands without constricting circulation to the fingers. A suitable material is 2 mil thick polyethylene film such as X-2000 by Pierson Industries. The diameters of the fingerholes 15 in inches are as follows: thumb 0.98, index finger 0.79, middle finger 0.87, ring finger 0.75 and pinky 0.63.

An annular quick connect and disconnect assembly 20 is permanently sealed around the end of cuff section 14a and removably sealed with an adhesive 22 to the abdominal skin around protector/retractor 12. Referring to FIGS. 3–6 assembly 20 includes interconnecting upper and lower seal rings 20a and 20b, preferably molded of a medical grade flexible, slightly resilient thermoplastic rubber of Shore 80A hardness such as Santoprene® made by Advanced Elastomer Systems. Upper ring 20a defines an annular collar 24 permanently sealed around the periphery of cuff section 14a with an upwardly facing annular bead 26 concentrically disposed around collar 24.

Figure 3:
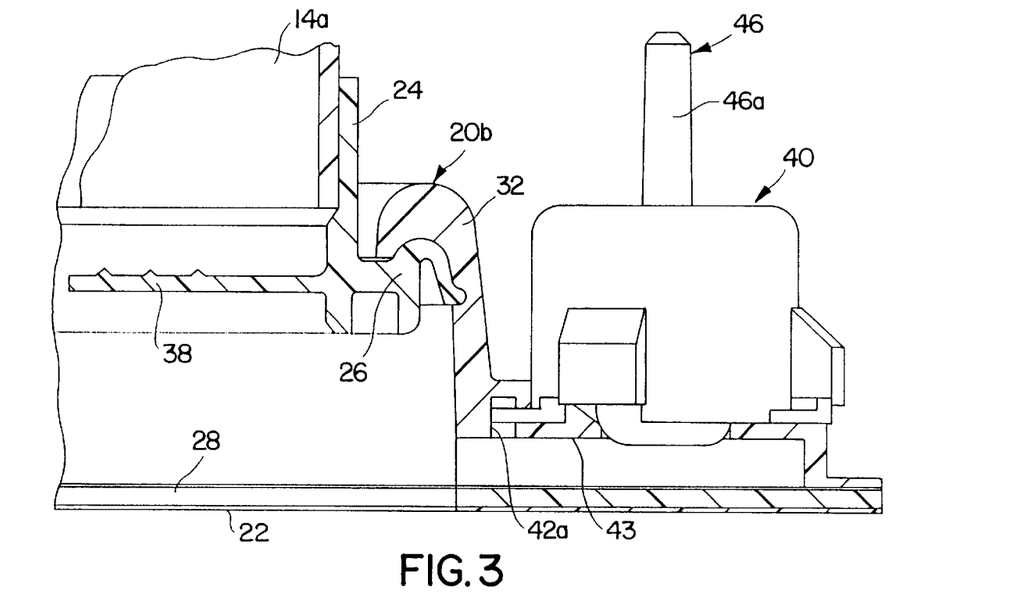
FIG. 3 is a more detailed view, partially in cross section, of a segment of a connect and disconnect assembly shown connected in the enclosure of FIG. 1.
Figure 4:
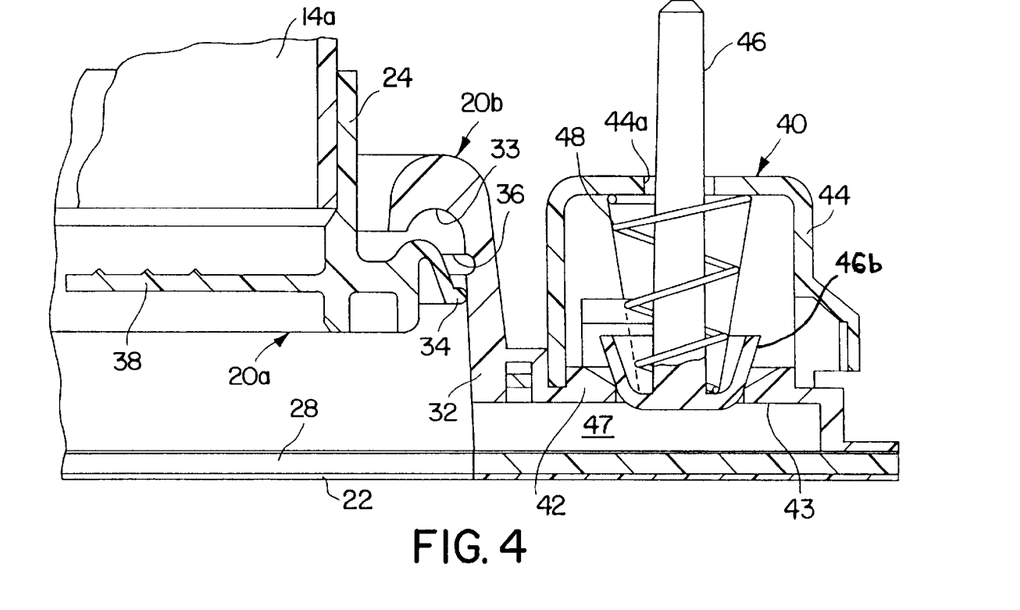
FIG. 4 is a cross sectional view like FIG. 3 with the assembly shown disconnected.
Figure 5:
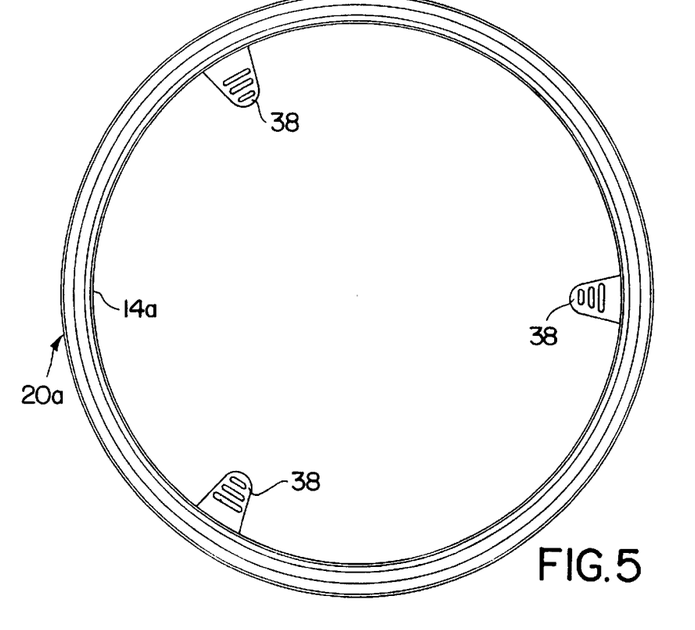
FIG. 5 is a view in cross section of an upper seal ring of the enclosure taken along the line 5—5 of FIG. 2.

Lower ring 20b includes an annular flange 28 with adhesive 22 for applying ring 20b during surgery. A peel strip 30 (FIG. 2) covers the adhesive until the ring is to be applied to the skin of the abdomen. A preferred adhesive is IT8-59-A by Tolas Health Care Packaging of Feasterville, Pa. An annular member 32 sealed around the bottom to flange 28 extends upward and terminates in a downwardly facing annular groove 33 formed to interface in a tight seal with bead 26 of upper ring 20a. An annular detent 34 extending radially from bead 26 snaps into an annular groove 36 on the inner surface of member 26b when bead 26 and groove 33 are positively engaged as shown in FIG. 3. Pull tabs 38 extending inward from cylinder 24 enable the surgeon's fingers to pull detent 34 inward and disengage from groove 36 thereby releasing upper ring 16a from lower ring 20b as shown in FIG. 4.

Figure 6:
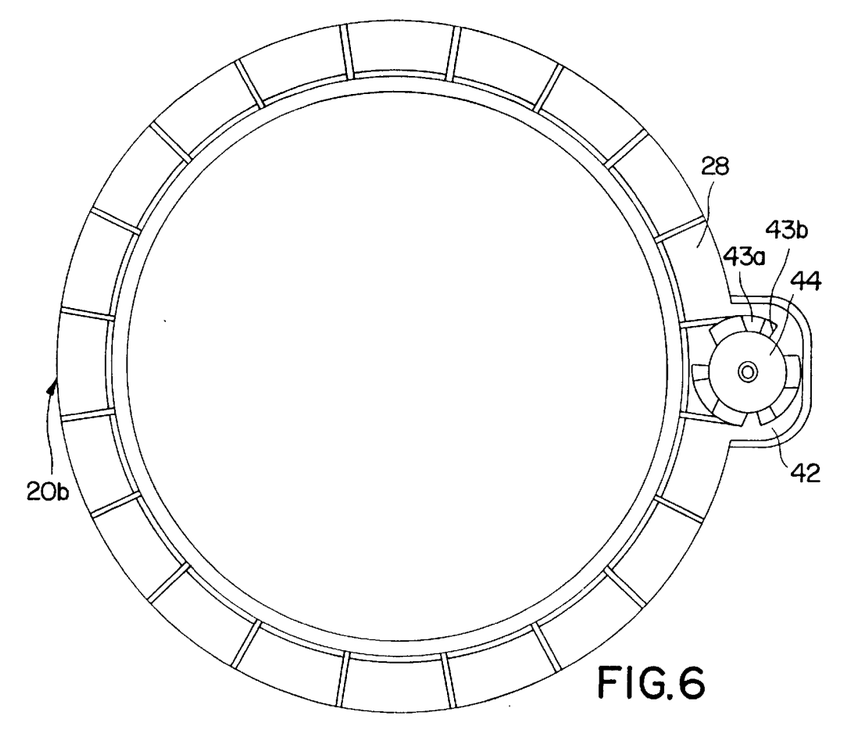
FIG. 6 is a plan view of a lower seal ring with an integral relief valve of the enclosure.

Lower ring 20b further includes a normally closed gas relief valve 40 for limiting the pressure in the abdominal cavity. It comprises a seat 42 integrally molded in the periphery of lower ring 20b, a cap 44, a poppet valve 46, and a helical spring 48. Cap 44 is secured to ring 16b by turning it about its cylindrical axis until tabs 43a on the bottom edge mate with slots 43b around seat 42. An aperture 44a in the top of cap 44 guides a stem 46a of plunger 46 onto seat 42 as well as serves as a vent for sufflation gas released through valve 40. Spring 48, around stem 46a between the top of cap 44 and a head 46b of plunger 46 urges valve 40 to a normally closed position. A recess 43 in the surface beneath seat 42 forms a channel 47 with flange 28 for continuously communicating between valve 40 and the abdominal cavity when lower seal ring 20b is adhered to the surface of the abdomen. If the cavity pressure exceeds a safe limit for pneumoperitoneum, e.g. 30 mm Hg, plunger 46 lifts off of seal 42 against the force of spring 48 to release the gas. The materials of construction for cap 44 and plunger 46 are preferably a rigid thermoplastic polycarbonate of Shore 80C hardness.

Figure 10:
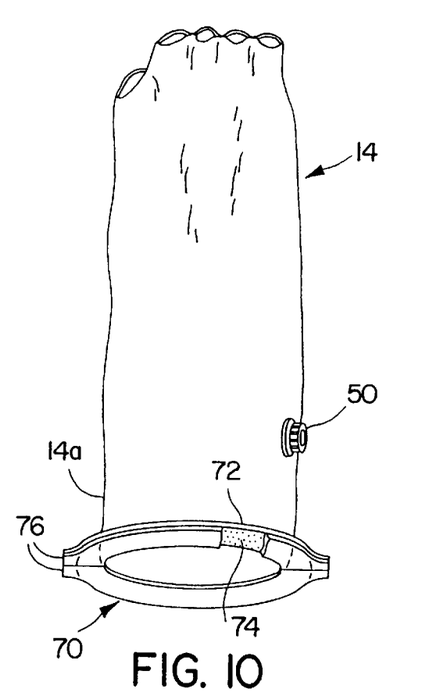
FIG. 10 is a perspective view of an enclosure similar to the embodiment of FIG. 1 but for a simplified connect and disconnect assembly.
Figure 11:
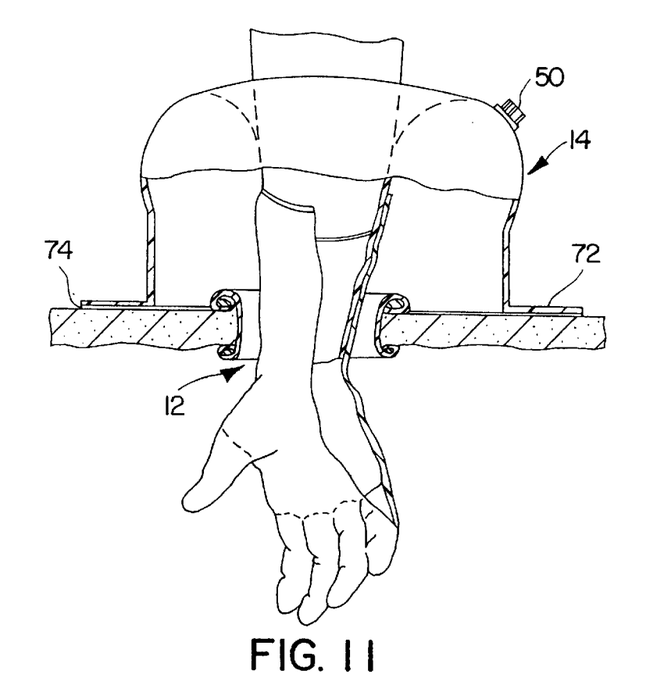
FIG. 11 is an elevation view of the enclosure of FIG. 10 in an operating position.

FIGS. 10 and 11 represent a simplified annular quick connect and disconnect assembly 70 for glove 14. The assembly includes a annular flange 72 of flexible plastic permanently heat-sealed or bonded around the end of cuff section 14a. An adhesive 74 is coated on the bottom side of flange 72 for applying to the skin or a surgical drape around the site of the incision. Complementary peelable strips 76 around respective halves of the flange cover the adhesive until the glove is attached to the skin or drape. A preferred material for flange 72 is a 4 mil plastic laminate of EVA/Surlyn®/EA, and a preferred adhesive is IT8-59-A supra.

Figure 7:
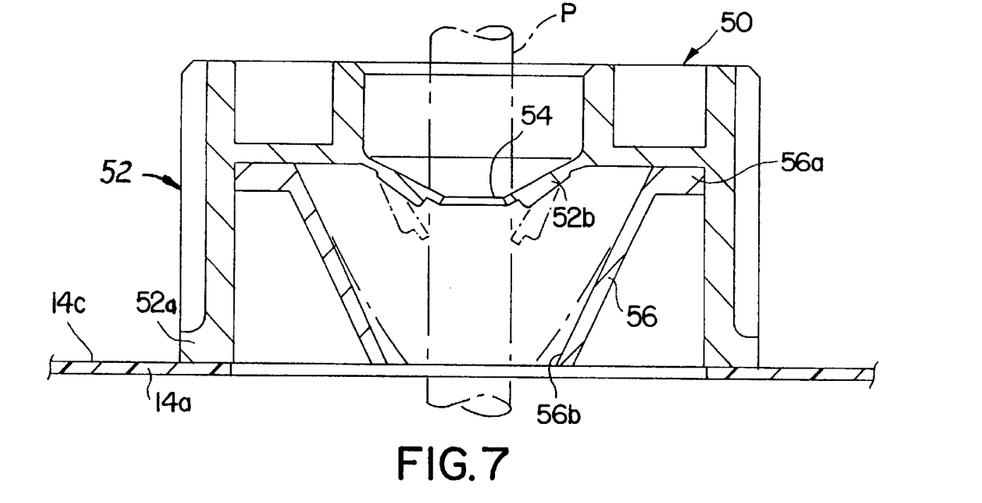
FIG. 7 is a view in cross section of an instrument port shown in the enclosure of FIG. 1.
Figure 8:
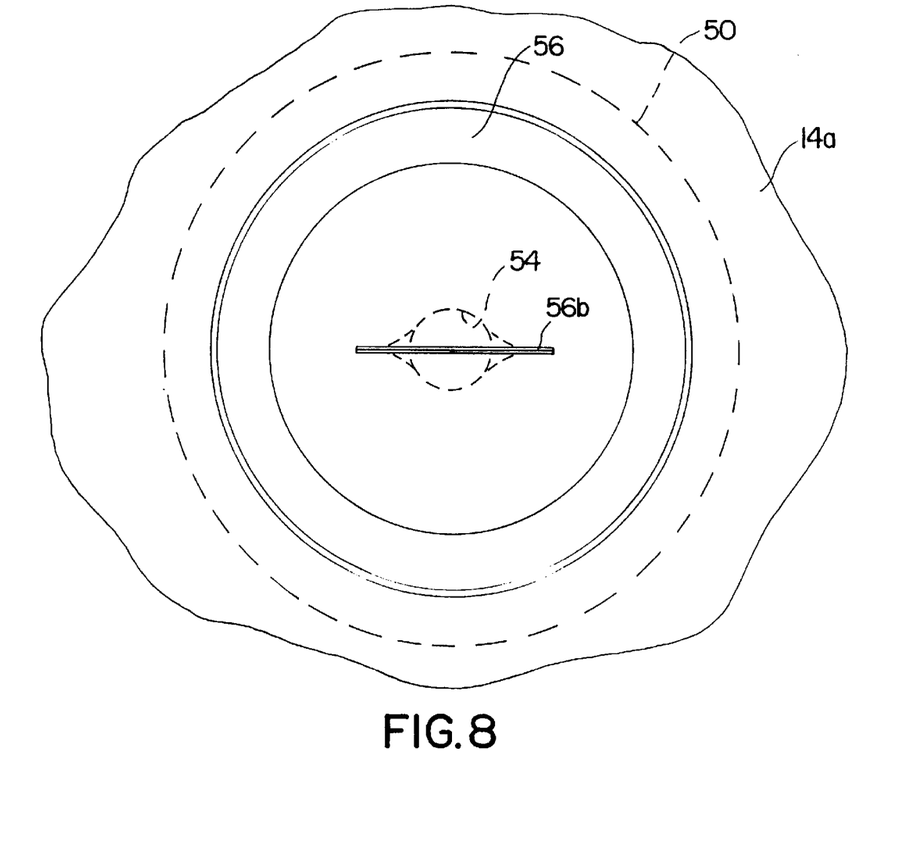
FIG. 8 is a view of the instrument port of FIG. 7 view from within the enclosure of FIG. 1.

Glove 14 includes an instrument port 50 located in cuff section 14a as an optional entry into the abdominal cavity for instruments such as graspers, staplers, clip appliers, scopes, etc. Referring to FIGS. 7 and 8, port 50 includes a generally cylindrical housing 52 with a flanged base 52a at one end secured to the inner side 14a of cuff section 14b. The other end defines a cone-shaped wall 52b tapering along its conical axis into the housing to a circular hole 54 at the small end which is sized for slidably receiving an instrument without leakage. A duckbill valve 56 prevents pressure loss when no instrument is present in port 50. It comprises a flanged base 56a at one end secured to the inside of the housing 52 adjacent to wall 52b. The other end tapers to a normally closed slit 56b spaced below hole 54 in a plane transverse to the conical axis of wall 50b. Housing 50 and insert 52 must have sufficient resilience for wall 50b to form a gas-tight seal around the instrument's surface and to ensure that slit 56a closes tightly after the instrument is withdrawn. A suitable material found for this purpose is a molded thermoplastic rubber such as Santoprene® by Advanced Elastomer Systems.

Figure 9:
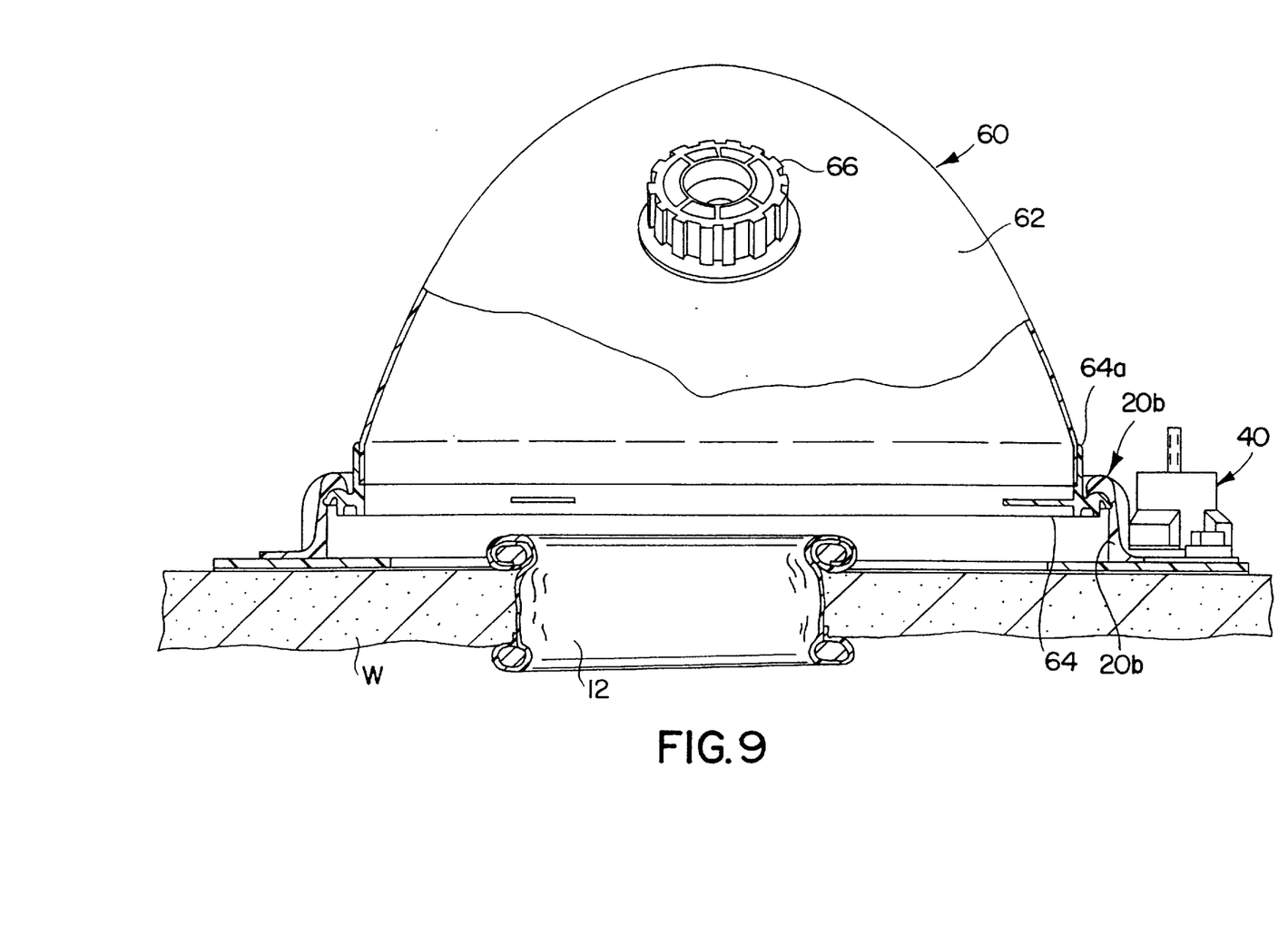
FIG. 9 is a view in elevation and partial cross section of an extracorporeal pneumoperitoneum enclosure according to another embodiment of the invention as applied during an interruption of a surgical procedure.

FIG. 9 illustrates an alternate embodiment of an extended pneumoperitoneum enclosure 60 according to the invention for use in place of the glove enclosure 10 during interruptions in surgery conducted under pneumoperitoneum conditions. It comprises a dome-shaped envelope 62 of thin transparent flexible polyethylene film and an upper seal ring 64 of like construction as upper seal ring 20a. The perimeter at the open base is sealed around upper seal ring 64 and interconnects with lower seal ring 20b of assembly 20. Of course enclosure 60 may also include its own lower seal ring. Access by surgical instruments is provided by an instrument port 66, like port 50, secured to envelope 62.

A method according to the invention for performing hand-assisted abdominal laparoscopic surgery utilizing the extended pneumoperitoneum enclosures as above-described is as follows. The site for making the incision is precisely traced on the abdomen of the patient. In the embodiment of FIGS. 1–8, seal ring 20b and glove 14 are preferably separated from upper seal ring 20a and put on by the surgeon's hand before ring 20a is attached to the abdomen in order to afford a more clear unobstructed view of the tracing. Peel strip 30 covering adhesive 22 on lower ring 20b is removed and the ring adhered to the abdomen around the tracing.

Guided by the tracing, a small muscle-splitting incision is made through the abdomen wall sufficient in size to allow the surgeon's hand to pass through. The peritoneum is incised roughly the same amount. Wound liner and retractor 12 is installed in the incision to protect the wound from contamination and to spread it apart for easier access by the hand. The abdomen wall and peritoneum may also be punctured at other locations for receiving an insufflator, a laparoscope and other instruments.

Wearing an inner surgical glove 16, the surgeon dons glove 14 by placing his/her hand into fingerless hand section 14b until the thumb and fingers extend completely through fingerholes 15 and become snugly sealed thereby. Cuff section 14a and upper ring 20a (or assembly 70 of FIG. 10) are drawn up over the forearm exposing the outer side 14d of fingerless section 14a. For added protection against leakage around holes 15, an outer surgical glove 18 is preferably placed over the exposed finger portions of inner glove 16 and hand section 14a. If preferred, the surgeon may don the glove 14 and attach it to the lower ring 20b before incising the abdomen.

Cuff section 14a is then inverted with the facing inside out and upper ring 20a is sealed in lower ring 20b by pressing bead 26 into recess 33 until detent 34 of upper ring 20a snaps into groove 36 of lower ring 20b. The abdominal cavity and the annular envelope formed by glove 14 may now be insufflated to the desired pressure either through a separate cannula or through port 50 in glove 14. The gloved hand may thereafter enter and re-enter the abdominal cavity as often as necessary during the surgery without losing pneumoperitoneum. Any increase in insufflating gas pressure, such as caused by a sudden reduction in volume when inserting the hand, is prevented by pressure relief valve 40.

Should an extended interruption in a surgical procedure be needed but still maintaining pneumoperitoneum, glove 14, attached to upper seal ring 20a, may be disconnected leaving in place lower seal ring 20b. Dome-shaped envelope 62, attached to upper seal ring 64, may then be connected to lower seal ring 20b and insufflation restored.

Of course, when using the embodiment of FIGS. 10 and 11, the surgeon would don the glove 14, peel strips 76 from the adhesive 74 and place the flange directly on the skin or surgical drape around the incision site after the wound liner and retractor 12 was installed.

Some of the many advantages and novel features of the invention should now be readily apparent. For example, an extracorporeal pneumoperitoneum enclosure is provided which can be continually worn by the surgeon during hand-assisted laparoscopic surgery under conditions of pneumoperitoneum without loss of dexterity. It allows the surgeon to quickly disconnect and reconnect the enclosure from the patient while still retaining it on his/her hand. An alternate embodiment provides a dome-like enclosure which can be substituted for the glove whenever a protracted interruption in medical procedure is necessary. It enables minimal invasive surgery and risk of damage to a patient's immune system. Due to the smaller incisions, shorter healing time and less time for recuperation in the hospital is possible. The enclosures are also relatively simple in design and easy to use.

It will be understood, of course, that various changes in the details, materials, steps and arrangement of parts which have been herein described and illustrated in order to explain the nature of the invention may be made by those skilled in the art within the principle and scope of the invention as expressed in the appended claims.

We claim:

1. Apparatus for providing extracorporeal pneumoperitoneum around a surgical incision in a patient, comprising, in combination:

a flexible gas impermeable envelope having a first cuff section with an opening and a second hand section with holes respectively aligned for enabling the thumb and fingers of a hand to extend through said holes said envelope being elongate between said hand section holes and said cuff opening for extending along a hand and forearm of a surgeon in a reversely turned manner when operatively connected to the patient; and a connecting assembly for securing said first cuff section around the incision, said connecting assembly having a first ring fixed in sealing contact with the periphery of said opening and a second ring for selectively connecting in sealing contact with said first ring; and a peelable adhesive fixed to said second ring for adhering it in sealing contact with skin around the incision.

2. Apparatus according to claim 1 wherein said holes are sized to seal gas tightly around the thumb and each finger.

3. Apparatus according to claim 1 further comprising:
a bead formed in said first ring around said opening; and
a groove formed in said second ring for interengaging with said bead.

4. Apparatus according to claim 3 further comprising:
detent means formed in said first and second rings for interlocking when said bead and said groove are fully engaged.

5. Apparatus according to claim 1 further comprising:
pressure relief means carried on said second ring in communication with said envelope for venting insufflated gas pressure exceeding a pre-selected limit.

6. Apparatus according to claim 5 wherein said preselected pressure limit is approximately 30 mm Hg.

7. Apparatus according to claim 1 further comprising:
an aperture in said first section;
port means fixed to said first section and formed to admit an elongate cylindrical instrument through said aperture while maintaining extracorporeal pneumoperitoneum.

8. Apparatus according to claim 7 wherein said port means further includes:
a generally cylindrical housing fixed to the inner side of said first section with a conical wall tapering inward to form a circular hole for slidably receiving an elongate surgical instrument;
a duckbill valve secured to said housing having a normally closed slit spaced below said hole in a plane transverse to a conical axis of said wall for slidably receiving the instrument in series with said hole.

9. Apparatus according to claim 8 wherein: said housing has sufficient resilience for said hole
to form a gas-tight seal around the instruments surface; and
said duckbill valve has sufficient resilience for said slit to close tightly upon itself when the instrument is withdrawn therefrom.

10. Apparatus for hand-assisted minimally invasive surgery under conditions of pneumoperitoneum, comprising:
a gas and fluid impermeable flexible glove-like envelope having a fingerless hand section terminating in holes respectively aligned for complete insertion through the holes of the thumb and fingers of the hand, and an elongate cuff section extending from said hand section and terminating in an opening for receiving said hand section when said cuff section is inverted with its inside facing out;
a connecting assembly secured to said glove-like envelope, said connecting assembly having a first ring fixed in sealing contact with the outer periphery of said opening and a second ring releasably connected in sealing contact with said first ring; and a peelable adhesive fixed to said second ring for adhering said glove-like envelope, with said cuff section inverted, in sealing contact with skin around an abdominal incision and forming thereby an annular enclosure in sealed communication with the incision.

11. Apparatus according to claim 10 wherein said holes are sized to seal gas tightly around the thumb and each finger.

12. Apparatus according to claim 10 further comprising:
a bead formed in said first ring around said opening; and
a groove formed in said second ring for interengaging with said bead.

13. Apparatus according to claim 12 further comprising:
detent means formed in said first and second rings for interlocking when said bead and said groove are fully engaged.

14. Apparatus according to claim 10 further comprising:
valve means integral with said second ring communicating with said glove for venting insufflated gas pressure exceeding a preselected limit.

15. Apparatus according to claim 14 wherein said preselected pressure limit is approximately 30 mm Hg.

16. Apparatus according to claim 10 further comprising:
an aperture in said cuff section; and
port means fixed to said cuff section formed to admit an elongate cylindrical instrument through said aperture while maintaining extracorporeal pneumoperitoneum.

17. Apparatus according to claim 16 wherein said port means further includes:
a generally cylindrical housing fixed to the inner side of said cuff section with a conical wall tapering inward to form a circular hole for slidably receiving an elongate surgical instrument; and
a duckbill valve secured to said housing tapering inward to a normally closed slit spaced below said hole in a plane transverse to the conical axis of said wall for slidably receiving the instrument in series with said hole.

18. Apparatus according to claim 17 wherein
said housing has sufficient resilience for said hole to form a gas-tight seal around the instrument's surface; and
said duckbill valve has sufficient resilience for said slit to close tightly upon itself when the instrument is withdrawn therefrom.

19. A method for performing hand-assisted minimally invasive abdominal surgery under conditions of pneumoperitoneum, comprising the steps of:
incising the abdomen and pneumoperitoneum;
donning a first conventional surgical glove on the hand;
placing the hand in a fingerless hand section of a second glove having thumb and finger holes with the thumb and fingers extending in sealed relation through said thumb and finger holes in the hand section; and
inverting a cuff section of the second glove inside out and around the hand section and securing said cuff section around the incision to form an enclosure communicating with the abdominal cavity; and
sufflating the abdominal cavity and enclosure.

20. A method according to claim 19 further comprising the step of:
after placing the hand in the second glove, donning a third surgical glove over the first and second gloves.

21. Apparatus for use in providing extracorporeal pneumoperitoneum around a surgical incision in a patient, comprising:

continuous flexible envelope having a distal portion for covering a surgeon's hand and a proximal portion for covering the surgeon's forearm, said proximal portion defining an opening for insertion of the surgeon's hand and forearm, said distal portion having a plurality of openings for receiving a surgeon's fingers and thumb and sealing about them when the surgeon's hand is placed in envelope with his fingers and thumb extending through said openings thereof, and means for releasably gas-tightly securing said proximal end portion opening to the patient around the surgical incision with said proximal glove end portion being reversibly turned to extend along the surgeon's forearm when operatively secured to the patient and insufflated.

22. Apparatus according to claim 21 wherein said envelope is formed of supple, non-elastic, plastic which conforms, but does not continuously constrict, about the bases of the fingers and thumb when the envelope is installed and the surgeon's hand clasped.

23. Apparatus according to claim 22 wherein said plastic material is a polyethylene film.

24. Apparatus according to claim 22 wherein the diameters of said openings, in inches, are as follows: thumb 0.98, index finger 0.79, middle finger 0.87, ring finger 0.75 and pinky 0.63.

25. Apparatus according to claim 20 wherein said proximal end gastight sealing means includes ring means adapted to be adhesively secured to the patient around the incision.

26. Apparatus according to claim 25 wherein said ring means includes an annular base adhesively secured to the patient and an annular ring releasably engageable with said base.

27. Apparatus according to claim 26 wherein said annular ring matingly engages interiorly of said base in gastight relation therewith.

28. Apparatus according to claim 26 including a pressure relief value carried by said annular base for relieving overpressures.

29. Apparatus according to claim 26 including a dome having a self-sealing instrument port releasably engageable with said annular base for affording selective engagement of either said dome or said envelope on said base.

30. Apparatus according to claim 27 wherein said annular ring has at least one inwardly-extending pull tab affording disengagement of said ring from said base.

* * * * *

UNITED STATES PATENT AND TRADEMARK OFFICE
CERTIFICATE OF CORRECTION

PATENT NO. : 5,853,395

DATED : December 29, 1998

INVENTOR(S) : Berwyn M. Crook, et al.

It is certified that error appears in the above-identified patent and that said Letters Patent is hereby corrected as shown below:

Column 7, line 51, "instruments" should read --instrument's--;

Column 9, line 4, before "continuous" should be inserted --a--.

Signed and Sealed this

Thirteenth Day of April, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,853,395
DATED : December 29, 1998
INVENTOR(S) : Berwyn M. Crook et al It is certified that error appears in the above-indentified patent and that said Letters Patent is hereby corrected as shown below:

Column 10, line 1, "20" should be changed to read --21--;

Column 10, line 12, "value" should be changed to read --valve--.

Signed and Sealed this

Twenty-eighth Day of December, 1999

Attest:

Q. TODD DICKINSON

*Attesting Officer*                *Acting Commissioner of Patents and Trademarks*